United States Patent [19]
Lee et al.

[11] Patent Number: 5,776,181
[45] Date of Patent: Jul. 7, 1998

[54] EXPANDABLE STENT

[75] Inventors: J. Michael Lee, Halifax; Katherin H. Crewe; Christine Mastrangelo, both of Etobicoke, all of Canada

[73] Assignee: MedStent Inc., Rexdale, Canada

[21] Appl. No.: 687,223

[22] Filed: Jul. 25, 1996

[30] Foreign Application Priority Data

Jul. 25, 1995 [GB] United Kingdom ............ 9515282
Mar. 15, 1996 [GB] United Kingdom ............ 9605486

[51] Int. Cl.$^6$ ........................................ A61F 2/06
[52] U.S. Cl. ........................................ 623/1
[58] Field of Search ................ 623/1, 11, 12; 606/191, 194

[56] References Cited

U.S. PATENT DOCUMENTS

| | | | |
|---|---|---|---|
| 4,503,569 | 3/1985 | Dotter | 3/1.4 |
| 4,553,545 | 11/1985 | Maass et al. | 128/341 |
| 4,580,568 | 4/1986 | Gianturco | 128/345 |
| 4,655,771 | 4/1987 | Wallsten | 623/1 |
| 4,665,918 | 5/1987 | Garza et al. | 128/343 |
| 4,733,665 | 3/1988 | Palmaz | 128/343 |
| 4,856,516 | 8/1989 | Hillstead | 128/343 |
| 5,104,404 | 4/1992 | Wolff | 623/1 |
| 5,197,978 | 3/1993 | Hess | 623/1 |
| 5,201,757 | 4/1993 | Heyn et al. | 606/198 |
| 5,217,483 | 6/1993 | Tower | 606/198 |
| 5,226,913 | 7/1993 | Pinchuk | 623/1 |
| 5,344,426 | 9/1994 | Lau et al. | 606/198 |
| 5,354,308 | 10/1994 | Simon et al. | 606/198 |
| 5,356,423 | 10/1994 | Tihon et al. | 606/198 |
| 5,389,106 | 2/1995 | Tower | 606/198 |
| 5,395,390 | 3/1995 | Simon et al. | 606/198 |
| 5,397,355 | 3/1995 | Marin et al. | 623/12 |
| 5,405,377 | 4/1995 | Cragg | 623/1 |
| 5,405,380 | 4/1995 | Gianotti et al. | 623/1 |
| 5,433,723 | 7/1995 | Lindenberg et al. | 606/198 |
| 5,443,499 | 8/1995 | Schmitt | 623/1 |
| 5,443,500 | 8/1995 | Sigwart | 623/1 |
| 5,449,373 | 9/1995 | Pinchasik et al. | 606/198 |
| 5,476,505 | 12/1995 | Limon | 623/1 |
| 5,476,508 | 12/1995 | Amstrup | 623/1 |
| 5,478,349 | 12/1995 | Nicholas | 606/198 |
| 5,507,767 | 4/1996 | Maeda et al. | 606/198 |
| 5,507,768 | 4/1996 | Lau et al. | 606/198 |
| 5,507,771 | 4/1996 | Gianturco | 623/1 |
| 5,514,176 | 5/1996 | Bosley, Jr. | 623/1 |
| 5,534,007 | 7/1996 | St. Germain et al. | 606/108 |
| 5,540,712 | 7/1996 | Kleshinski et al. | 606/198 |
| 5,549,635 | 8/1996 | Solar | 606/198 |
| 5,549,662 | 8/1996 | Fordenbacher | 623/1 |
| 5,556,414 | 9/1996 | Turi | 606/198 |
| 5,562,697 | 10/1996 | Christiansen | 623/1 |
| 5,562,725 | 10/1996 | Schmitt et al. | 623/1 |
| 5,571,135 | 11/1996 | Fraser et al. | 606/198 |
| 5,575,816 | 11/1996 | Rudnick et al. | 623/1 |
| 5,591,196 | 1/1997 | Marin et al. | 606/198 |
| 5,591,197 | 1/1997 | Orth et al. | 623/1 |
| 5,591,198 | 1/1997 | Boyle et al. | 606/198 |
| 5,591,229 | 1/1997 | Parodi | 623/1 |
| 5,593,434 | 1/1997 | Williams | 623/1 |
| 5,593,442 | 1/1997 | Klein | 623/1 |
| 5,601,593 | 2/1997 | Freitag | 606/198 |
| 5,603,722 | 2/1997 | Phan et al. | 606/198 |
| 5,607,467 | 3/1997 | Froix | 623/1 |
| 5,618,300 | 4/1997 | Marin et al. | 606/198 |
| 5,626,602 | 5/1997 | Gianotti et al. | 606/198 |
| 5,626,603 | 5/1997 | Venturelli et al. | 606/198 |

FOREIGN PATENT DOCUMENTS

| | | |
|---|---|---|
| 0 540 290 A2 | 5/1993 | European Pat. Off. . |
| 9503010 | 2/1995 | WIPO .................. 623/1 |
| WO 95/09584 | 4/1995 | WIPO . |
| WO 96/09013 | 3/1996 | WIPO . |

*Primary Examiner*—Michael J. Milano
*Assistant Examiner*—Tram Anh T. Nguyen
*Attorney, Agent, or Firm*—Fried, Frank, Harris, Shriver & Jacobson

[57] ABSTRACT

A stent has a tubular body with longitudinal struts interconnected by multi-bar linkages. The struts inhibit foreshortening of the body and relative rotation between the links in the linkages permits radial expansion. The links are plastically deformed as they are expanded to maintain the expanded diameter.

61 Claims, 14 Drawing Sheets

EXPANDABLE STENT

BACKGROUND OF THE INVENTION

Expandable stents are widely used to provide local reinforcement in fluid-carrying vessels within the human body. The stent is essentially a cylindrical member which may be expanded radially to dilate the vessel and to provide support for the wall of the vessel to maintain it in the dilated condition.

In order to insert the stent, it has previously been proposed to place the stent into the vessel on an expandable or balloon catheter. With the stent positioned at the appropriate location, the catheter is inflated and the stent is caused to expand radially against the wall of the vessel. Once the stent is expanded to the required diameter, the catheter is deflated and may be removed, leaving the stent in position.

The stent must of course remain expanded against the wall of the vessel and should be capable of withstanding the forces imposed by the wall of the vessel. Moreover, the stent should be able to negotiate tight turns in the arterial system during placement while minimizing damage to the arterial wall.

A number of different mechanisms have been proposed to permit the expansion of the stent, including devices which reorient the components forming the stent so that they may adopt a greater overall diameter.

In another class of stents, as typified by the stent shown in U.S. Pat. No. 4,733,665 to Palmaz, the stent is configured to be plastically deformable so that after expansion it retains the increased diameter. In the Palmaz stent, the plastic deformation is provided by means of an open-mesh diamond structure. As the catheter is expanded, the intersecting members of the mesh deform so that the stent adopts an increased diameter.

With the arrangements shown in the Palmaz stent and similar configurations, a radial expansion of the stent is accompanied by an axial foreshortening of the stent. The degree of foreshortening is predictable but the ultimate location of the stent along the vessel is not predictable. Thus, one end of the stent may remain stationary relative to the blood vessel so that the opposite end is subjected to the maximum axial displacement or there may be progressive foreshortening from both ends with an intermediate location remaining stationary. The foreshortening of the stent leads to an unpredictable location for the stent in its expanded condition and induces relative movement in an axial direction between the vessel wall and the stent which is generally undesirable.

SUMMARY OF THE INVENTION

It is therefore an object of the present invention to provide a stent in which the above disadvantages are obviated or mitigated.

In general terms, the present invention provides a stent in which a plurality of circumferentially-spaced longitudinal struts are interconnected by multi-bar linkages. Adjacent links of the linkages are angularly disposed to one another such that a radial force causes relative rotation between adjacent links to permit radial enlargement of the stent. The longitudinal struts inhibit foreshortening of the stent so that the final location of the stent can be predicted.

BRIEF DESCRIPTION OF THE DRAWINGS

Embodiments of the invention will now be described by way of example only with reference to the accompanying drawings, in which.

DESCRIPTION OF THE PREFERRED EMBODIMENTS

Figure 1:
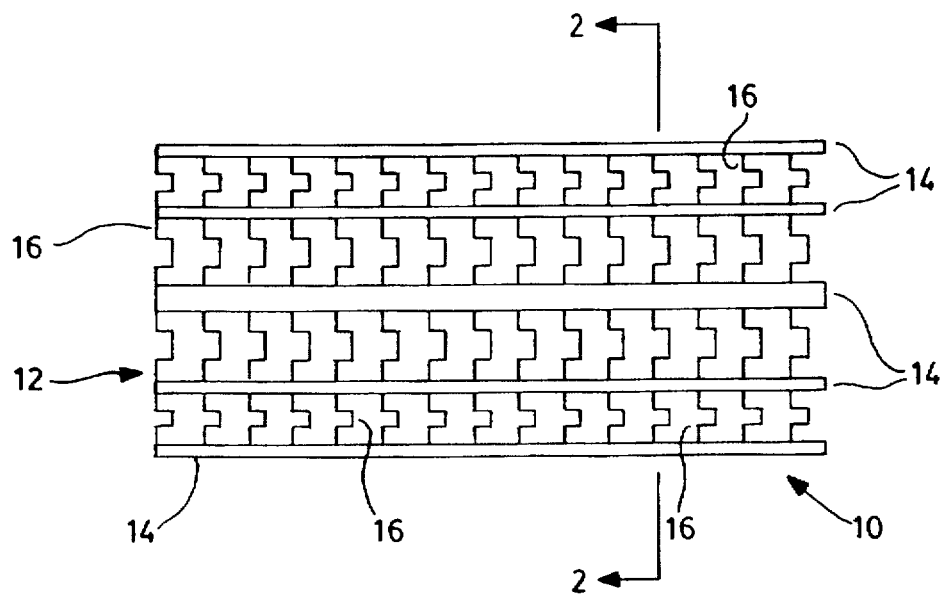
FIG. 1 is a side elevation of an assembled stent.
Figure 2:
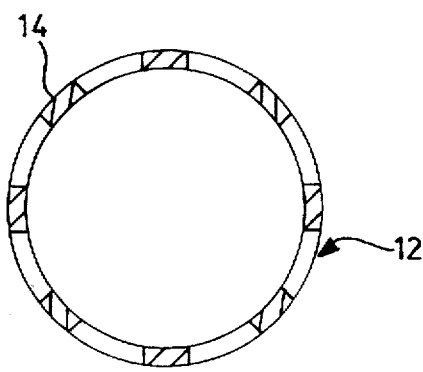
FIG. 2 is a view on the line 2—2 of FIG. 1.
Figure 3:
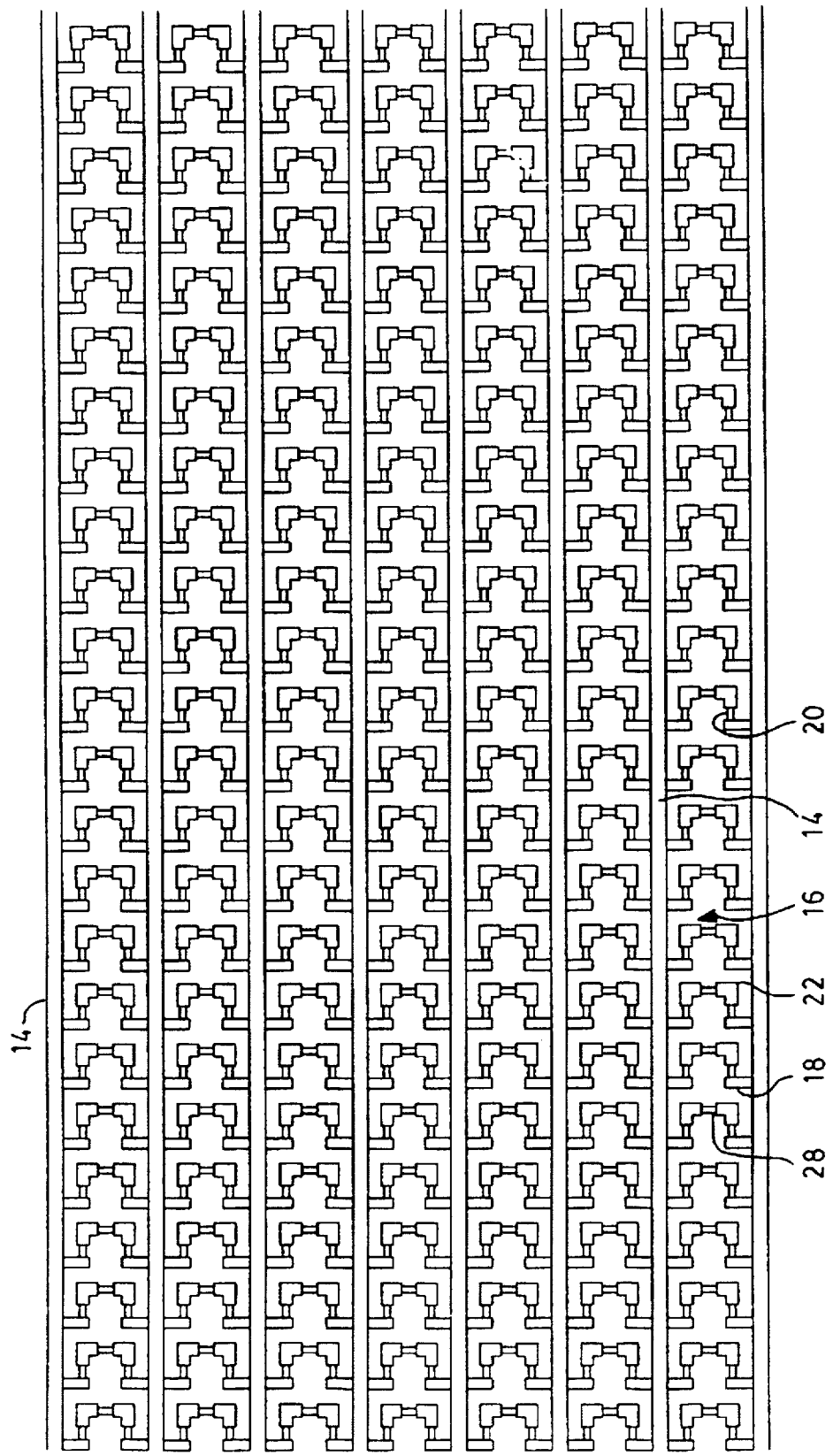
FIG. 3 is a developed view of the stent shown in FIG. 1.

Referring therefore to FIG. 1, a stent 10 has a generally tubular body 12 which is initially dimensioned to permit insertion into a vessel such as an artery. The body 12 includes a plurality of longitudinal struts 14 which are interconnected by multi-bar linkages 16. The linkages 16 are regularly spaced along the axial extent of the struts 14 and maintain struts 14 in circumferentially spaced relationship.

Figure 4:
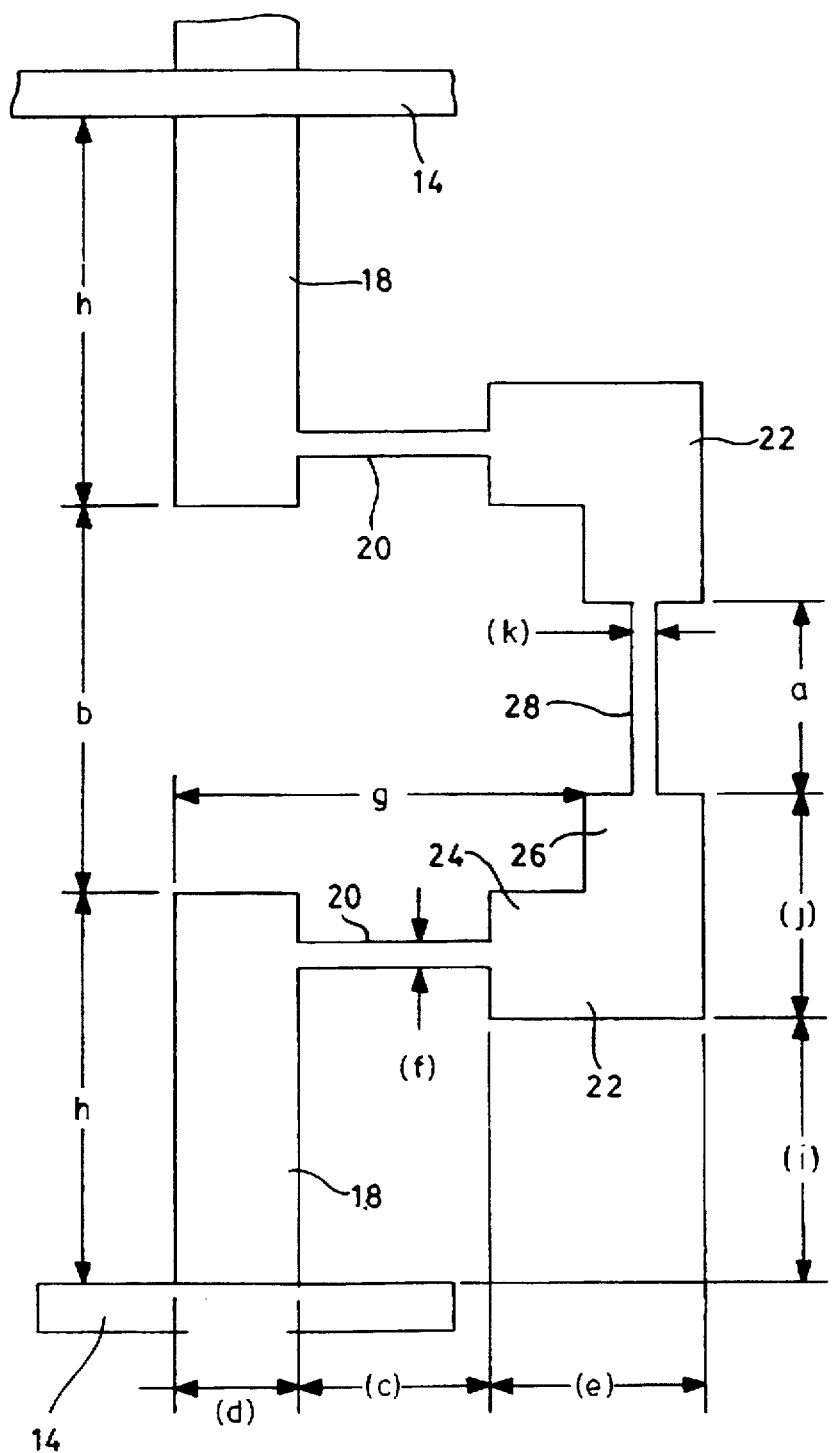
FIG. 4 is a view on an enlarged scale of a portion of the stent shown in FIGS. 1–3.

As can best be seen in FIG. 4, each of the linkages 16 includes a pair of oppositely directed circumferential links 18 with axial links 20 connected to the circumferential links 18 and extending parallel to the struts 14 but spaced therefrom. The axial links 20 are connected to an L-shaped corner link 22 which has an axial leg 24 and circumferential leg 26. The legs 26 of opposed corner links 22 are interconnected by a circumferential connecting link 28 to interconnect the adjacent struts 14. The links 18, 20, 22 and 28 of the linkage 16 are formed by removal of material from a seamless tube of bio-compatible material so that the links are integrally connected to one another. Typically such material would be a metal such as both pure and alloyed titanium, platinum, nitinol memory metals, gold or stainless steel, and the linkage may suitably be machined through micro machining techniques. Other materials could be used that are considered suitable for implantation including plastics materials having the requisite properties.

Each of the linkages 16 is similar and the relative dimensions between the links in each linkage determine the change in diameter for a given load. In a typical example, as shown in FIG. 4, taking the length of the connecting link 28 to be of unit length, then the relative dimensions of the other links as indicated by the letters or FIG. 4 are as follows:

| a | b | c | d | e | f | g | h | i | j | k |
|---|---|---|---|---|---|---|---|---|---|---|
| 1 | 2 | 1 | 0.625 | 1.125 | 0.125 | 2.125 | 2.0 | 1.375 | 1.125 | 0.125 |

Figure 15:
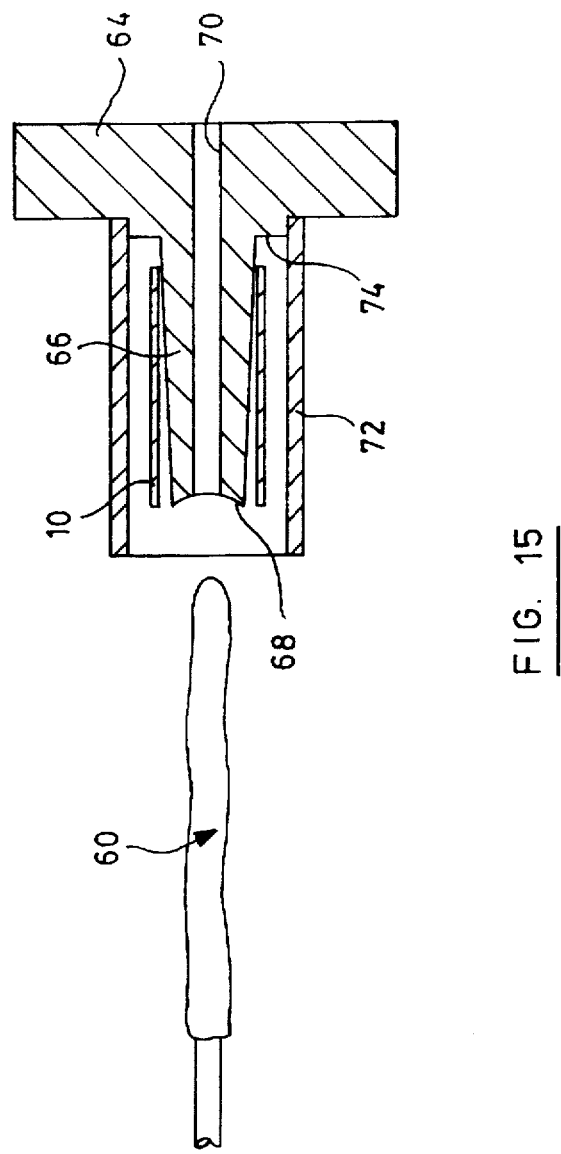
FIG. 15 is a sectional view of a stent support and catheter.

The stent 10 is typically inserted into the vessel by using a balloon catheter 60. The stent 10 is mounted on the catheter 60 shown in FIG. 15. To assist in placement of the stent 10 on the catheter 60, the stent is initially located on a support 62 that has a bar-like head 64 and a tapered body 66. The stent 10 is snugly received on the body 66 which has a concave recess 68 at one end to locate the tip of catheter 60. A bore 70 extends through the body 66 to accomodate a wire if the catheter is of the type that employs such.

A protective sleeve 72 is located over the body 66 and is retained on a boss 74 on the head 64. The sleeve 72 thus protects the stent 10 from extraneous external forces with the body 66 providing support for the stent 10 in transit.

To transfer the stent to the catheter 60, the sleeve 72 is removed and the body 66 is aligned with the catheter 60. The stent may then be slid axially from the body 66 over the catheter 60 and the support and sleeve discarded. In this way, the stent is guided during transfer and the placement of the stent on the catheter facilitated.

The recess 68 assists in locating and aligning the catheter 60 during transfer and of course the wire, if present, may be fed through the bore 70.

The stent 10 is located on the body 66 such that the links 28 are closer to the boss 74 than the associated links 18. Transfer of the stent 10 to the catheter thus ensures that the stent 10 is oriented on the catheter 60 such that the connecting link 28 of the linkage 16 is in advance of the circumferential links 18 during insertion of the stent 10 into the vessel.

The catheter is inserted into the vessel in a conventional manner until it is located at the stenosis.

After placement within the vessel, the catheter is then inflated to apply a radially expanding force to the stent.

Figure 5:
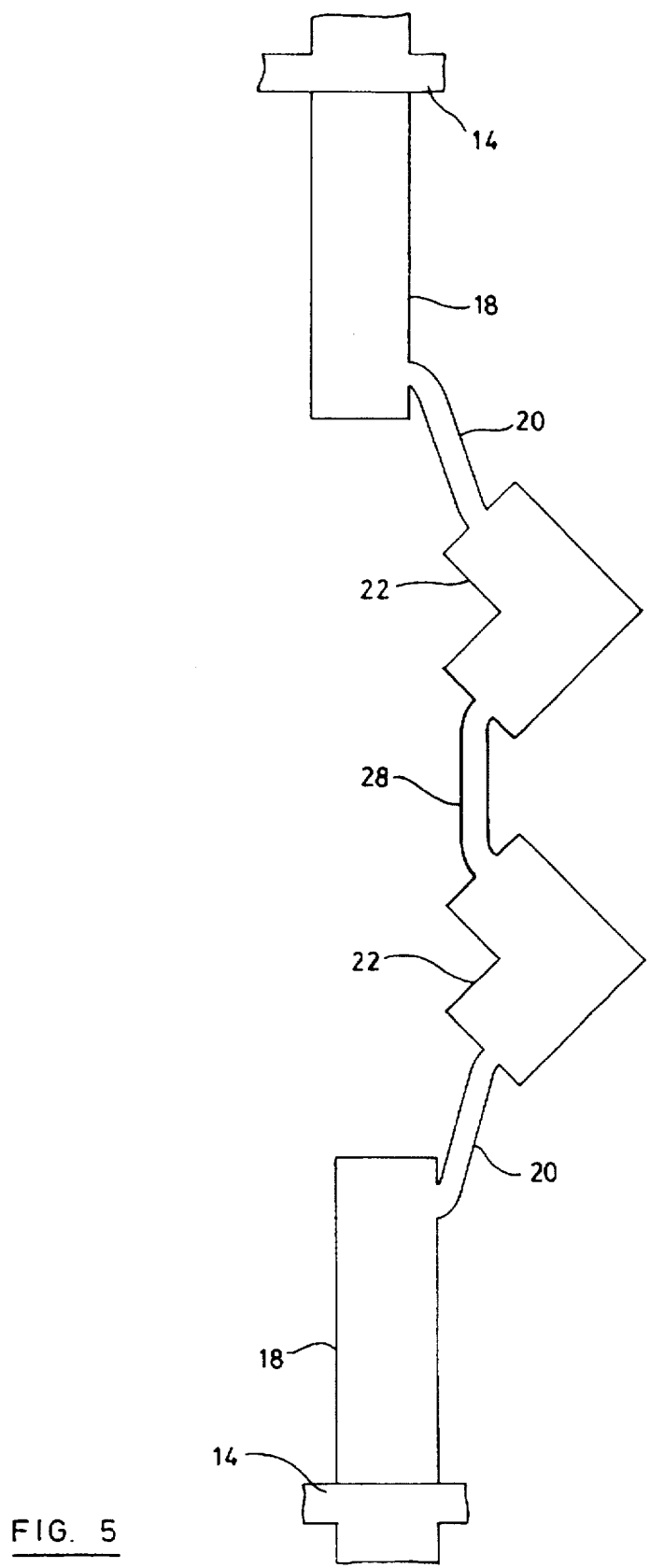
FIG. 5 is a view of the portion of the stent shown in FIG. 4 after radial expansion.

As shown in FIG. 5, the application of the radial force causes the circumferential spacing of struts 14 to increase. The circumferential links 18 are carried with the struts 14 and a hinging action occurs at the connection of the axial link 20 to both the circumferential link 18 and the corner link 22 by plastic deformation of the links. Similarly, the connecting link 28 hinges at its connection to the corner link 22 to provide a hinging action between the links. The links 22 is thus bodily rotated as the struts 14 are spread.

By virtue of the relatively narrow links 20, 22, the hinging at their junction to the larger links 18,22 exceeds the yield point of the material and causes a permanent deformation and increase in diameter. A pair of spaced hinge points is thus established and thus the total rotation required between the axial links 20 and circumferential link 28 is distributed between two locations.

The catheter is then deflated and removed, leaving the stent 10 in situ. It will be noted, however, that during inflation the struts 14 maintain the axial spacing between the circumferential links 18 so that the overall length of the stent remains the same with no relative axial movement between the vessel and the stent.

In tests with samples of the configuration of FIGS. 4 and 5, an extension from the spacing of the struts 14 was increased from an initial value of 6 units to 8.48 units upon application of loads consistent with those used in the expansion of such stents.

Figure 6:
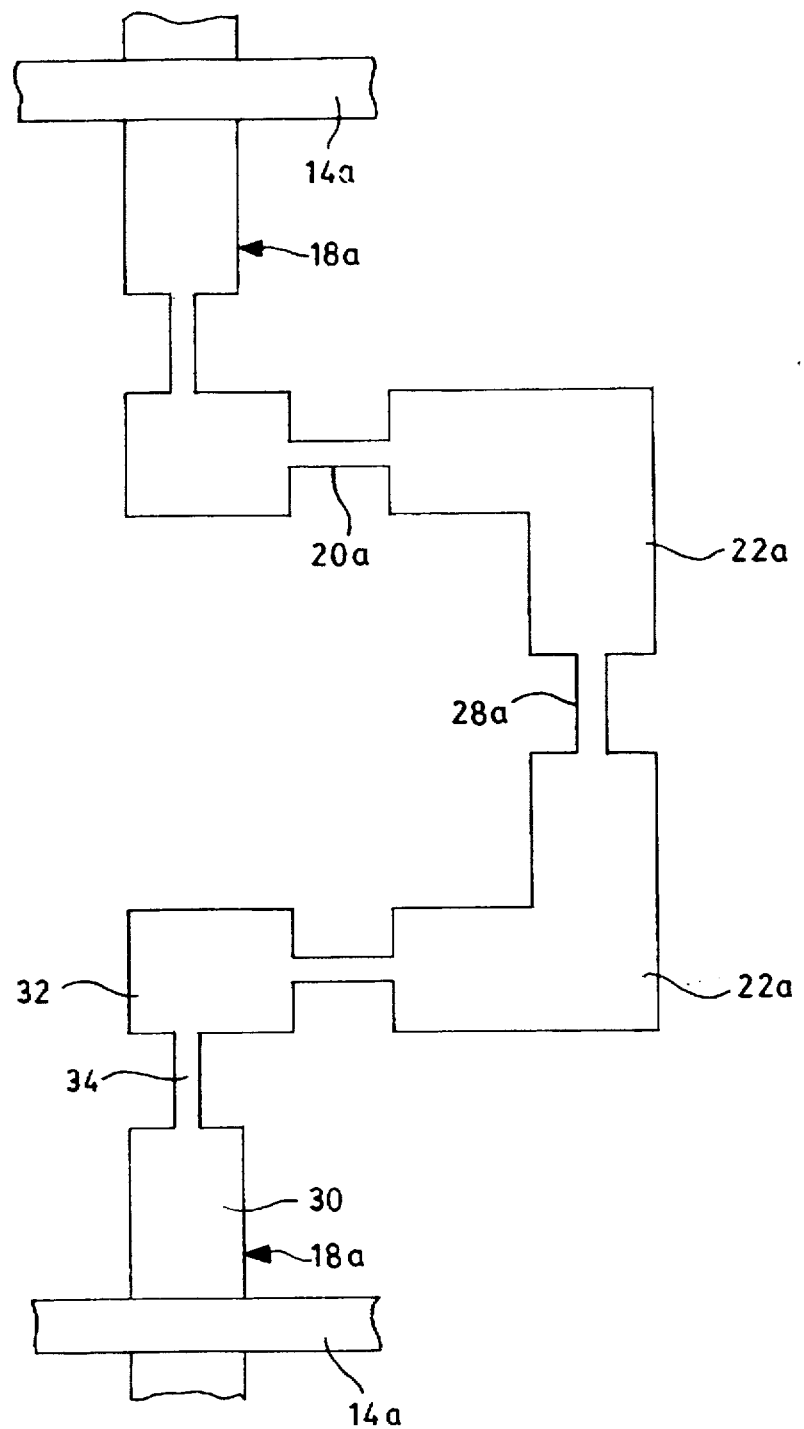
FIG. 6 is a view similar to FIG. 4 of an alternative embodiment of stent.
Figure 7:
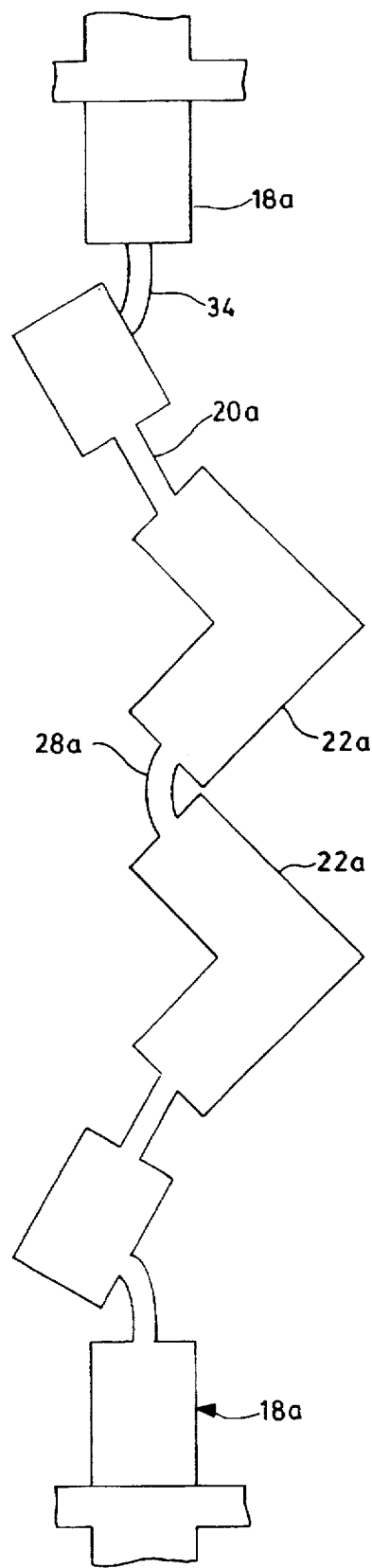
FIG. 7 is a view of the embodiment of FIG. 6 after radial expansion.

An alternative embodiment of linkage 16 is shown in FIGS. 6 and 7, in which like components will be denoted with like reference numerals with a suffix 'a' added for clarity.

In the embodiment of FIG. 6, the circumferential link 18a is formed as a pair of rectangular nodes 30,32 interconnected by a narrow bar 34. The length of the axial link 20a is reduced to 0.5 of a unit value and a corresponding reduction in the length of the connecting link 28 to 0.5 is made. As may be seen in FIG. 7, the application of the radial load causes the connection at the bar 34 to plastically deform, allowing rotation of the rectangular bar 32. The connecting link 28a is also subjected to bending load as well as plastic deformation at the connection to the links 22a.

In tests conducted with samples of the arrangements shown in FIGS. 6 and 7, the initial spacing of the struts 14 was increased to 8.5 units after application of a radial force consistent with that found in balloon catheters.

Figure 8:
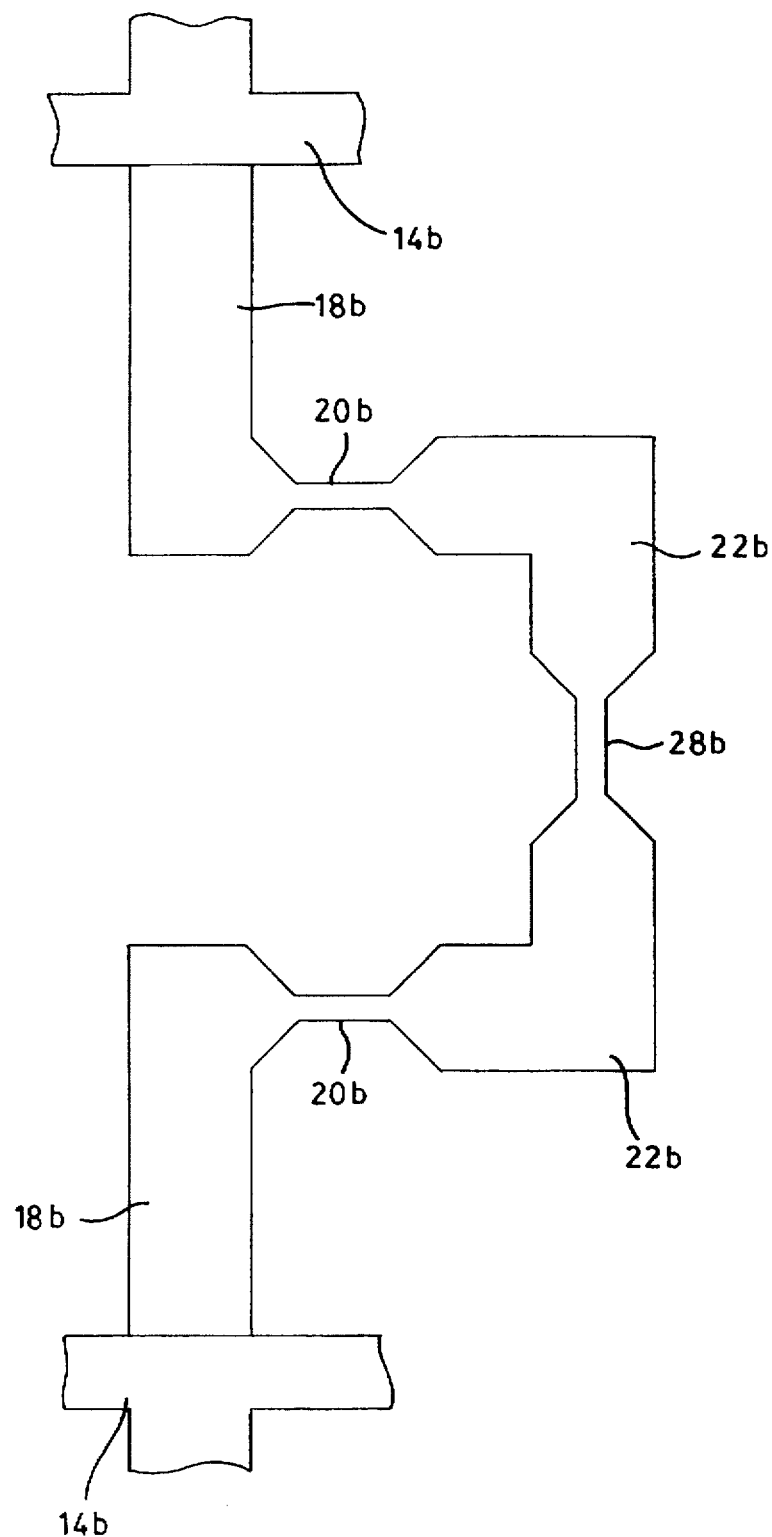
FIG. 8 is a further alternative of stent shown in FIG. 4.
Figure 9:
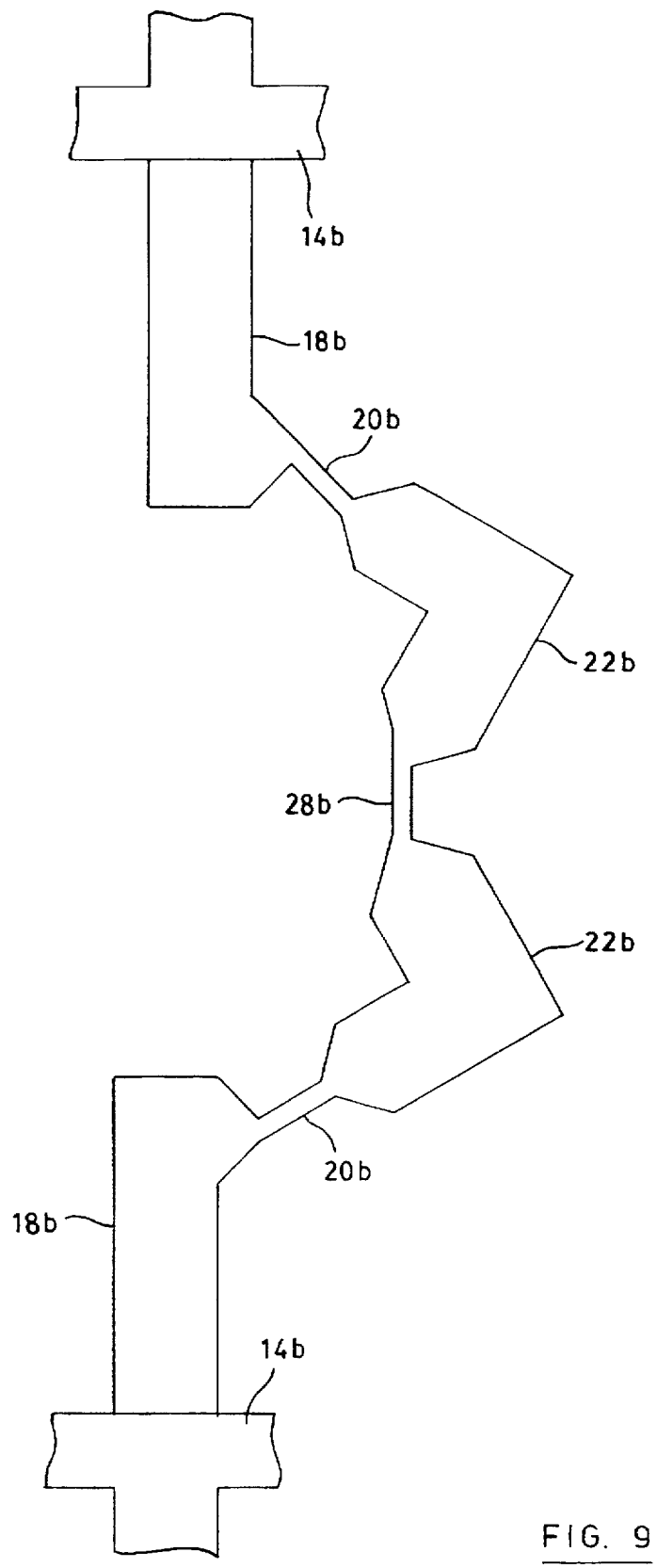
FIG. 9 is a view of the embodiment of FIG. 8 after radial expansion.

A further embodiment is seen in FIG. 8 where again like reference numerals will be used to denote like components with a suffix 'b' added for clarity. In the embodiment of FIG. 8, the connection between the connecting links 20b and the circumferential links 18b progressively tapers to the dimension F. In a similar manner, the junction between the connecting link 28b and the link 22b progressively tapers and in each case the overall length of the links 20b,28b is reduced from 1 unit value to 0.5 unit value. A tapering in the order of 45° is found to be appropriate.

Figure 10:
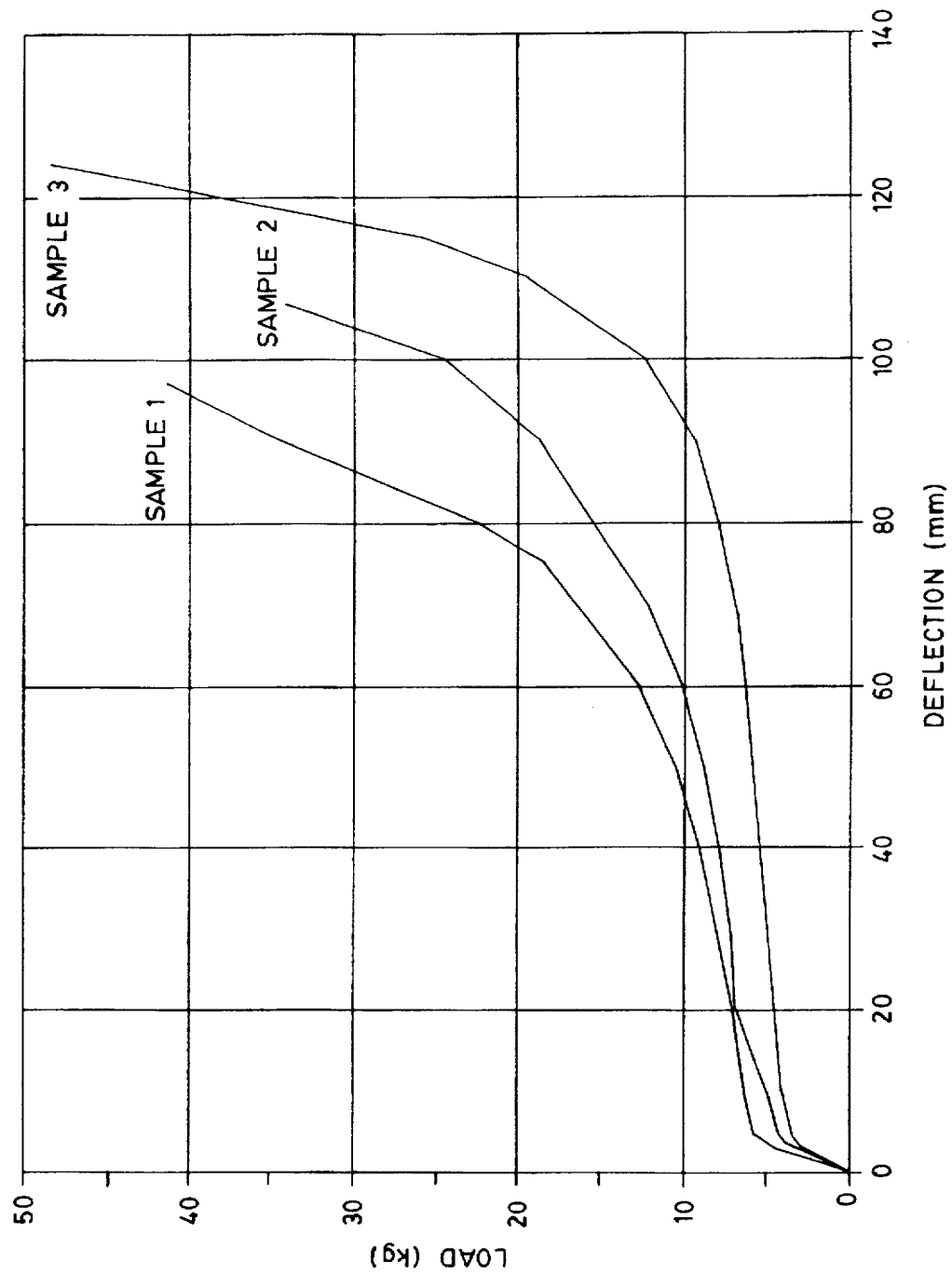
FIG. 10 is a comparative curve between the embodiments of stent shown in FIGS. 4, 6 and 8.

The results of tests conducted on the embodiment shown in FIGS. 4, 6 and 8 are represented on the curve of FIG. 10. This curve represents the applied radial load and the deflection obtained and it will be seen that in each embodiment there is an initial proportional increase of load and deflection followed by a much flatter curve indicating a plastic deformation. Thereafter, the load progressively increases, indicating that the orientation of the links is approaching a linear orientation. It will be seen that the embodiment of FIG. 8 provides a lower load to achieve the requisite deflections. With the provision of the relatively narrow links, it is possible to control the radial force necessary to expand the stent and the location at which the bending will occur. The force necessary to achieve radial expansion must be compatible with the forces available from a balloon catheter and the reduced width of the links permits this. Moreover, the plastic deformation of the narrow links maintains control of the orientation of the wider links during expansion.

A further embodiment is shown in FIGS. 11–14 offering enhanced flexibility for the stent during insertion, as may be needed to negotiate tight turns in the arterial system during placement, thereby minimizing damage to the arterial wall.

In the embodiment of FIGS. 11–14, in which like components are denoted with like numerals with a suffic "c" added for clarity, each of the struts 14c is segmented so as to be comprised of either a series of unitary struts 40 or a series of linking struts 42.

The unitary struts 40 alternate with linking struts 42 about the circumference of stent 10c and in the preferred embodiment an even number of each Is provided so that the linking struts 42 are diametrically opposed. It is preferred that four linking struts 42 are provided and are circumferentially spaced at 90° intervals.

Each of the unitary struts 40 extend between two of the linkages 16c so as to interconnect them. The unitary struts are spaced apart from one another by a gap indicated at 44 so that each linkage 16c is connected to only one of the adjacent linkages 16c. By contrast, the linking struts 42 extend between four of the linkages 16c and are then spaced from the next of the linking struts 42 by a space indicated at 46.

The gaps 44 between the unitary struts are circumferentially aligned to provide annular bands 48 whereas spaces 46 are staggered between alternate linking struts 42. Each of the linking struts 42 has a waist 50 to provide a region of enhanced flexibility in a plane tangential to the surface of the stent 10c. The waist 50 is aligned with one of the bands 48 and so provides the connection across the band 48 between the linkages 16c.

Figure 11:
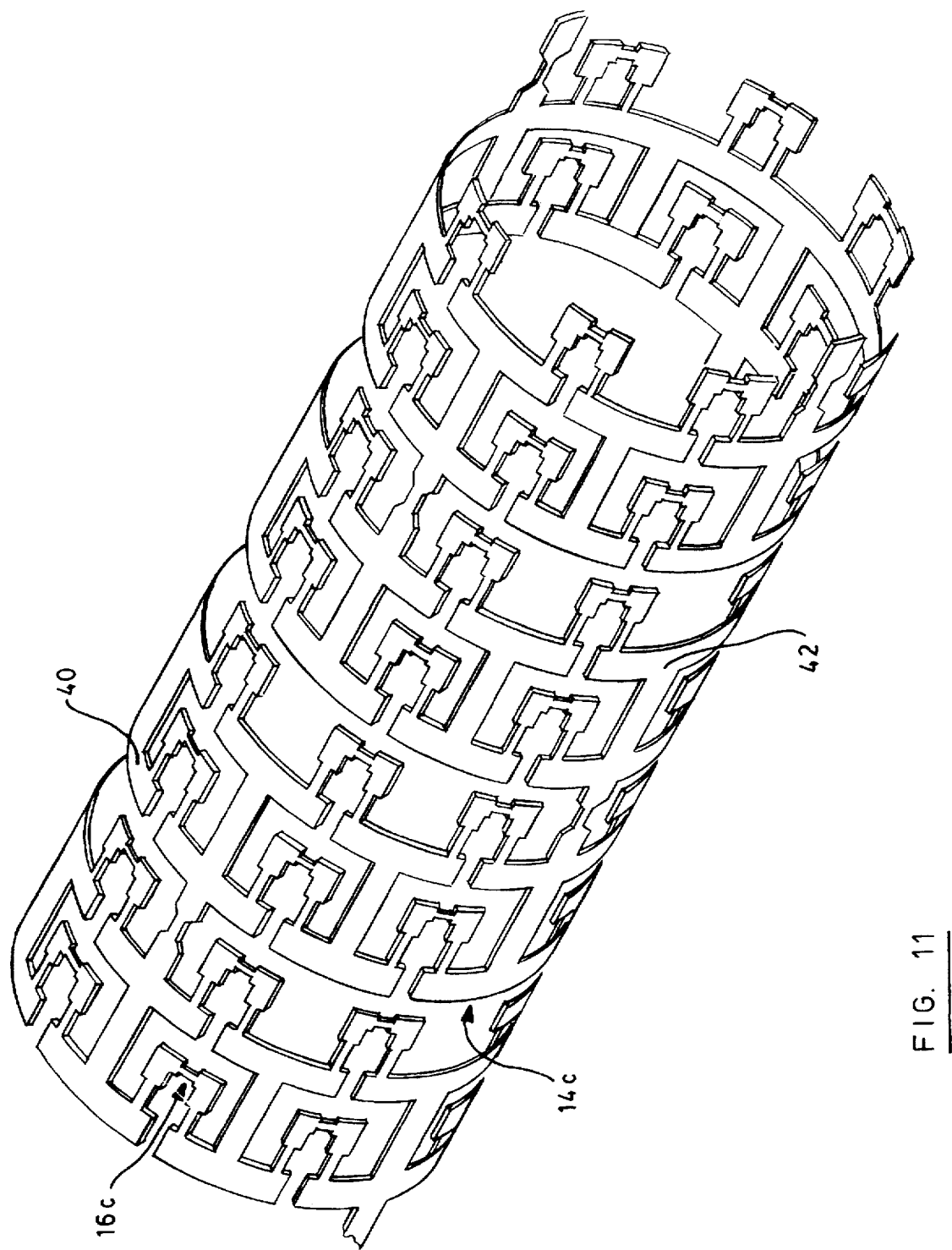
FIG. 11 is a perspective view of a further embodiment of stent.
Figure 12:
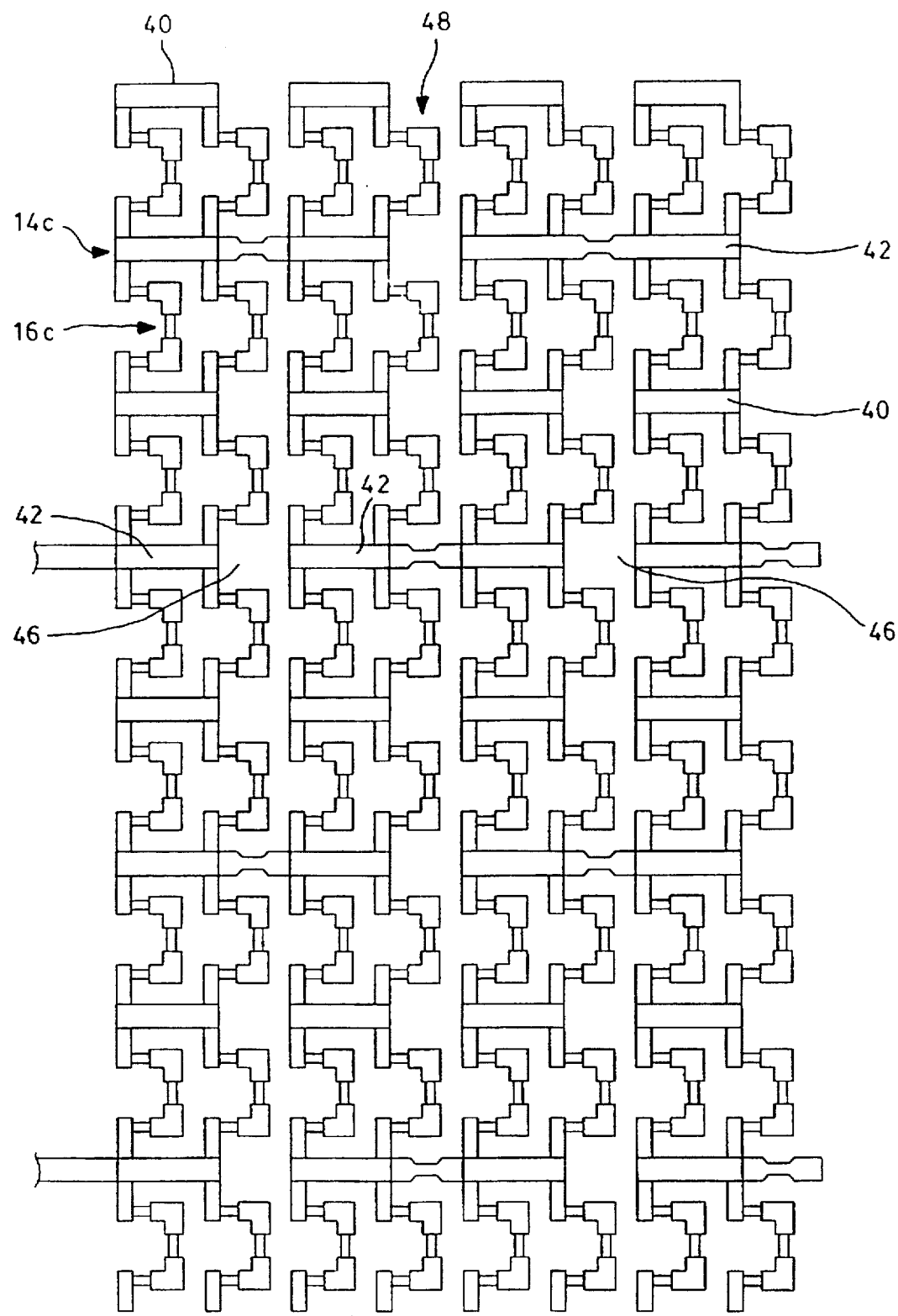
FIG. 12 is a developed view of the embodiment of stent shown in FIG. 11.

As can be seen in FIG. 11, the waists 50 are located at diametrically opposed locations it the respective bank 48 to define a pair of pivot axes X—X. By virtue of the staggered relationship between adjacent linking struts 42, the waists 50 are displaced by 90° in adjacent bands 48 so that the pivot axes X—X are disposed at 90°.

This arrangement provides flexibility about mutually perpendicular axially spaced axes allowing relative pivotal movement between sections of the stent to conform to the vessel into which it is inserted.

Figure 13:
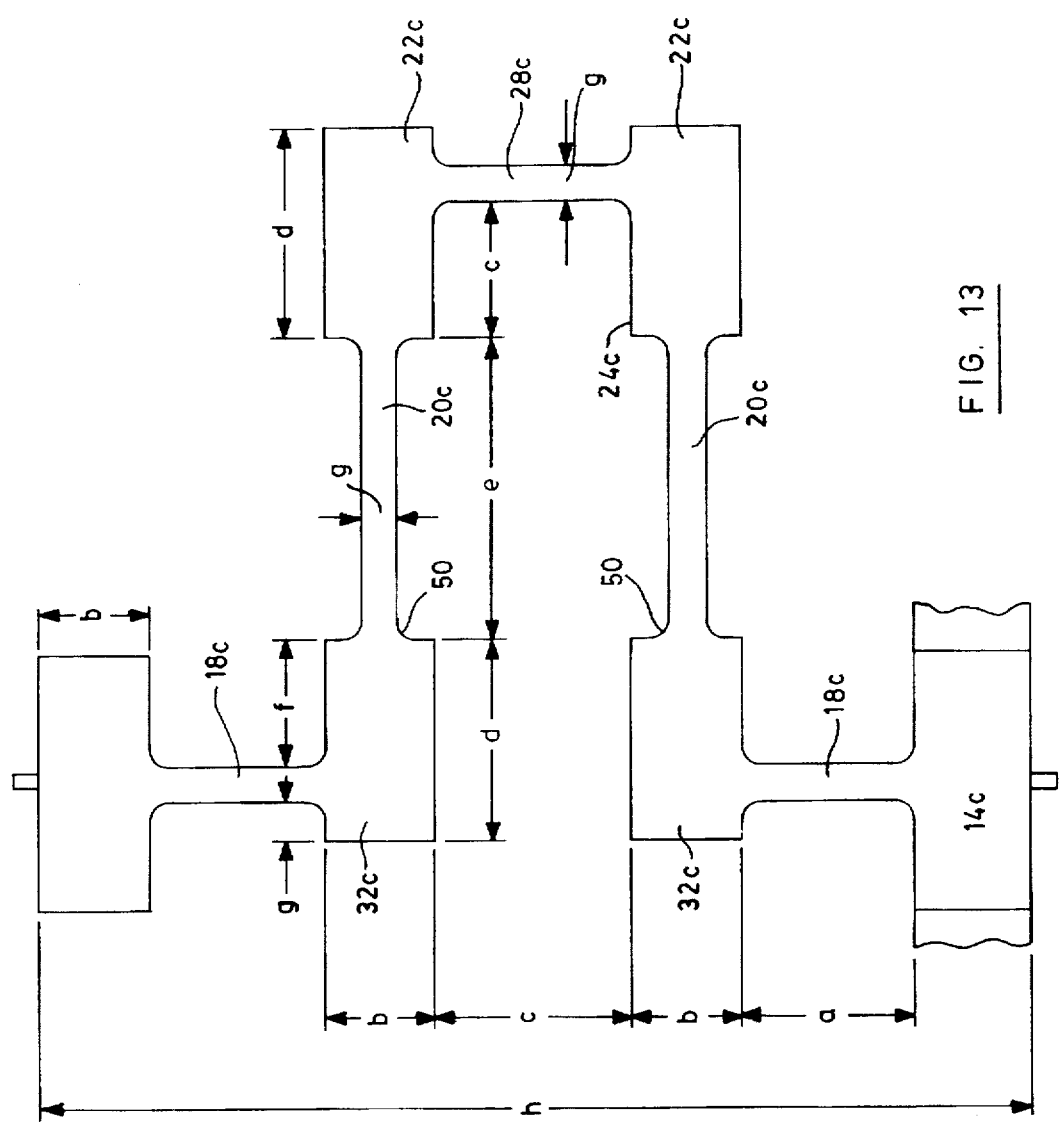
FIG. 13 is an enlarged view of a portion of the stent shown in FIG. 11.

The linkage 16c is shown in detail in FIG. 13 and includes circumferential links 18c and axial links 20c connected by a node 32c.

The circumferential link 28c is connected to axial link 20c by corner link 22c which is formed as a rectangular leg 24c.

It will be noted that the connection of each of the links 18c,20c,28c to the struts 14c, nodes 32c and corner link 22c by radiused fillets 52 that reduce local stress concentrations.

In one preferred example, the relative dimensions are as follows:

| a | b | c | d | e | f | g | h | i |
|---|---|---|---|---|---|---|---|---|
| 1.20 | 0.75 | 1.40 | 1.40 | 2.00 | 0.90 | 0.25 | 6.9 | 5.30 |

The fillets 52 are each 0.125 and the thickness of the material between 0.0625 and 0.125.

Figure 14:
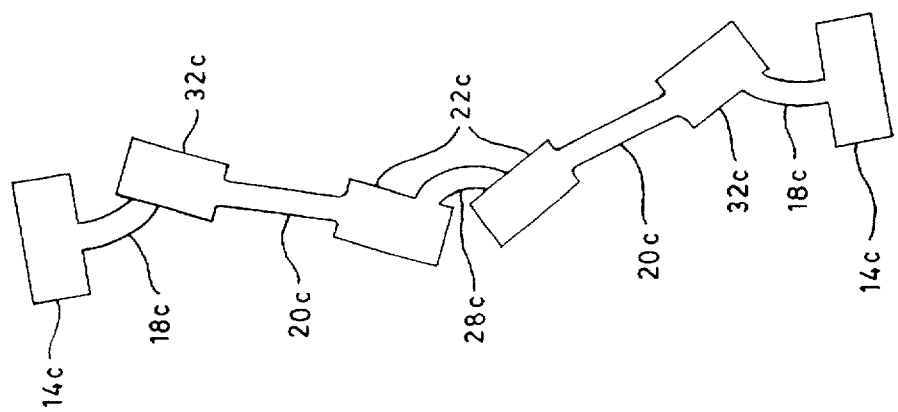
FIG. 14 is a view similar to FIG. 9 showing the stent after radial expansion.

With this configuration, the application of a radial load results in the circumferential expansion shown in FIG. 14 from which it can be seen that a uniform bending of the links 18c is obtained and that the axial links 20 have assumed a circumferential orientation.

Upon circumferential expansion, the linking struts 42 inhibit foreshortening as each band 48 has two axial struts that inhibit relative axial movement between adjacent linkages 16c. At the same time the relatively flexible waists 50 disposed at 90° to one another provides the requisite flexibility for insertion of the stent 10c.

Although the embodiment of FIG. 11 shows axes of rotation at 90° to one another, alternative arrangements may be used by varying the relative orientation of the waisted links. For example, by spacing the links at 60° angles, three axes of rotation are obtained at axially spaced locations.

The following relative dimensions of linkage 16 have also been found to provide satisfactory performance:
Example I:

| a | b | c | d | e | f | g | h | i |
|---|---|---|---|---|---|---|---|---|
| 10 | 7.5 | 11 | 17.8 | 38.6 | 12.3 | 3 | 46 | 74.2 |

Example II:

| a | b | c | d | e | f | g | h | i |
|---|---|---|---|---|---|---|---|---|
| 10.3 | 7.7 | 12.2 | 17.8 | 38.6 | 12.3 | 3 | 48.2 | 74.2 |

Example III:

| a | b | c | d | e | f | g | h | i |
|---|---|---|---|---|---|---|---|---|
| 10.0 | 7.5 | 11 | 14.3 | 20.4 | 9.2 | 3 | 46 | 49 |

In each of these examples, the units are 0.001 inches and the thickness of the material used was 0.003 inches.

In Examples I and III, the width, ie. circumferential dimension, of the struts 14 was 5 units and the axial spacing between adjacent linkages 16 was 12 units.

In Example II, the width of the struts 14 was 2.85 units and the axial spacing between adjacent linkages was 3 units.

In each case, the linkages are repeated 4 times about the circumference. The diameter of the stent prior to expansion was 65 units and after expansion with a 45° rotation of the links 20c an outside diameter of 197 units was obtained with Example II and 152.3 units with Example III. The axial spacing between linkages 16 was sufficient to permit the bodily rotation of the corner links as the stent expands radially. The provision of the strut 14 inhibits foreshortening and therefore ensures that the linkages can rotate as required.

Figure 16:
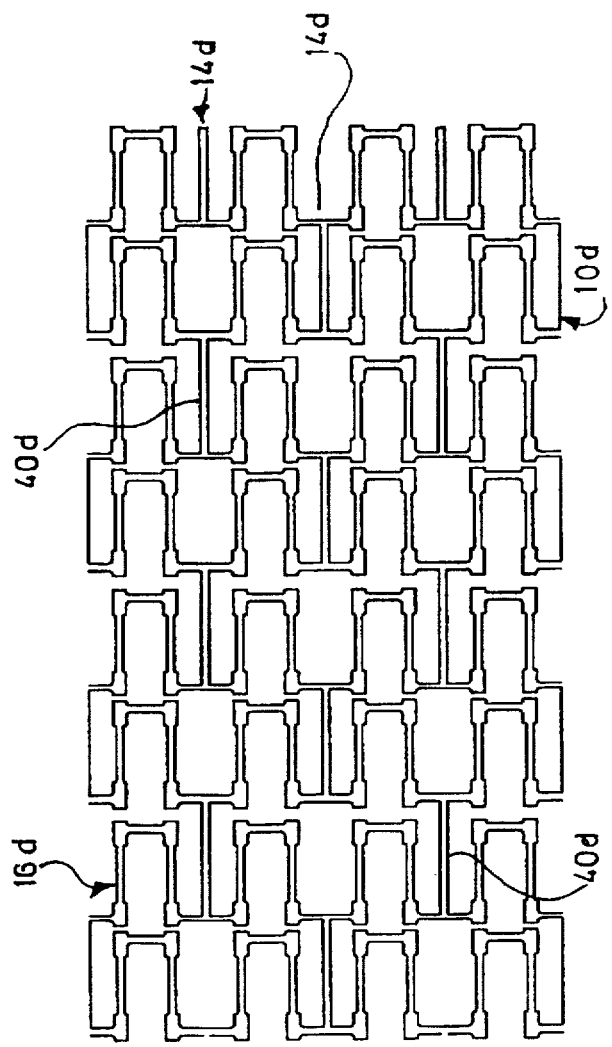
FIG. 16 is a developed view, similar to FIG. 12, of a further embodiment.

A further embodiment is shown in FIG. 16 in which like components will be identified with like reference numerals with a suffix 'd' added for clarity. The embodiment of FIG. 16 is similar to that shown in FIGS. 12 and 13. However, each of the struts 14d is segmented into a series of unitary struts 40d that extend between two adjacent linkages 16d. The struts 40d are staggered circumferentially to alternate the direction of connection between adjacent linkages. The unitary linkages 40d are thus aligned at diametrically opposed locations and thus define a pair of orthogonal axes at axially spaced locations to provide flexibility during insertion.

The stent will of course be dimensioned to fit within the intended vessel and engage the wall when extended. A typical stent for insertion in an artery will have a diameter of between 1.5 mm and 3.5 mm when inserted and may have a diameter of between 2 mm and 12 mm when expanded.

We claim:

1. A stent having a generally tubular body with a plurality of circumferentially spaced longitudinal struts extending parallel to a longitudinal axis of said body, circumferentially adjacent pairs of said struts being interconnected solely by a set of linkages axially spaced from one another and each including a plurality of links connected to one another, adjacent links of said linkages being angularly disposed relative to one another such that a radial force causes relative rotation between adjacent links and plastic deformation thereof to permit radial expansion of said stent, said struts inhibiting relative axial movement between said linkages and foreshortening of said body and said struts remaining in substantially parallel relationship with said longitudinal axis upon radial expansion of said stent and wherein all of said sets of linkages are unidirectionally facing with one of said links of each linkage being offset axially from the connection of said linkage to said struts in a common direction.

2. A stent according to claim 1 wherein each of said linkages comprises an opposing pair of first circumferentially extending links connected at one end to said struts and connected at an opposite end to axially extending links, said axially extending links being connected to each other by a second circumferentially extending link axially spaced from said first circumferentially extending links.

3. A stent according to claim 2 wherein the intersection of at least one pair of adjacent links of each of said linkages has a zone of relative weakness adjacent to but spaced from said intersection to provide a pair of spaced hinge points, whereby relative rotation between said at least one pair of links is distributed between said hinge points.

4. A stent according to claim 2 wherein said first circumferentially extending links and said axially extending links are enlarged at their intersections to provide a pair of spaced hinges at each connection thereof.

5. A stent according to claim 4 wherein said axially extending links and said second circumferentially extending link are enlarged at their intersections to provide a pair of spaced hinges at each connection thereof.

6. A stent according to claim 2 wherein said axially extending links are perpendicular to said first and second circumferentially extending links.

7. A stent according to claim 1 wherein each of said struts extends between at least two axially adjacent linkages.

8. A stent according to claim 7 wherein selected ones of said struts are discontinuous thereby providing a plurality of gaps along the length thereof, the axial location of said gaps being staggered about the circumference of said body whereby relative axial movement between said linkages is inhibited by struts circumferentially spaced from and axially aligned with said gaps.

9. A stent according to claim 8 wherein said struts axially aligned with said gaps are reduced in section to facilitate flexure thereof.

10. A stent according to claim 9 wherein struts having a reduced section are diametrically aligned to provide pivot axes of relative pivotal movement between said adjacent linkages.

11. A stent according to claim 10 wherein said pivot axes are angularly disposed relative to one another.

12. A stent according to claim 11 wherein said axes are disposed at 90° to one another.

13. A stent according to claim 10 wherein said axially extending links and said first and second circumferentially extending links are enlarged at their intersections to provide pairs of spaced hinges at each connection thereof.

14. A stent according to claim 13 wherein said enlarged intersections are generally rectangular.

15. A stent having a generally tubular body with a plurality of circumferentially spaced longitudinal struts extending parallel to a longitudinal axis of said body, circumferentially adjacent pairs of said struts being interconnected by a plurality of linkages axially spaced from one another and each including a plurality of links connected to one another, adjacent links of said linkages being angularly disposed relative to one another such that a radial force causes relative rotation between adjacent links and plastic deformation thereof to permit radial expansion of said stent, said struts inhibiting relative axial movement between said linkages and foreshortening of said body wherein each of said linkages comprises an opposing pair of first circumferentially extending links connected at one end to said struts and connected at an opposite end to axially extending links, said axially extending links being connected to each other by a second circumferentially extending link axially spaced from said first circumferentially extending links, and wherein said axially extending links and said first and second circumferentially extending links are enlarged at their intersections to provide pairs of spaced hinges at each connection thereof.

16. A stent according to claim 15 wherein said axially extending links are perpendicular to said first and second circumferentially extending links.

17. A stent according to claim 16 wherein said enlarged intersections are generally rectangular.

18. A stent according to claim 17 wherein each of said struts extends between at least two axially adjacent linkages.

19. A stent according to claim 18 wherein selected ones of said struts are discontinuous thereby providing a plurality of gaps along the length thereof, the axial location of said gaps being staggered about the circumference of said body whereby relative axial movement between said linkages is inhibited by struts circumferentially spaced from and axially aligned with said gaps.

20. A stent according to claim 19 wherein said struts axially aligned with said gaps are reduced in section to facilitate flexure thereof.

21. A stent according to claim 20 wherein struts having a reduced section are diametrically aligned to provide pivot axes of relative pivotal movement between said adjacent linkages.

22. A stent according to claim 21 wherein said pivot axes are angularly disposed relative to one another.

23. A stent according to claim 22 wherein said axes are disposed at 90° to one another.

24. A stent having a generally tubular body with a plurality of circumferentially spaced longitudinal struts extending along the entire length of and parallel to a longitudinal axis of said body, circumferentially adjacent pairs of said struts being interconnected by a plurality of linkages axially spaced from one another and each including a plurality of links connected to one another, adjacent links of said linkages being angularly disposed relative to one another such that a radial force causes relative rotation between adjacent links and plastic deformation thereof to permit radial expansion of said stent, said struts inhibiting relative axial movement between said linkages and foreshortening of said body, wherein selected ones of said struts are discontinuous thereby providing a plurality of gaps along the length thereof, the axial location of said gaps being staggered about the circumference of said body whereby relative axial movement between said linkages is inhibited by struts circumferentially spaced from and axially aligned with said gaps, and wherein selected ones of said struts have a reduced cross-section and are arranged such that a gap and a strut with a reduced cross-section lie in a common plane orthogonal to the longitudinal axis of said body.

25. A stent according to claim 24 wherein struts having a reduced section are diametrically aligned to provide pivot axes of relative pivotal movement between said adjacent linkages.

26. A stent according to claim 25 wherein said pivot axes are angularly disposed relative to one another.

27. A stent according to claim 26 wherein said axes are disposed at 90° to one another.

28. A stent according to claim 27 wherein each of said linkages comprises an opposing pair of first circumferentially extending links connected at one end to said struts and connected at an opposite end to axially extending links, said axially extending links being connected to each other by a second circumferentially extending link axially spaced from said first circumferentially extending links.

29. A stent according to claim 28 wherein said axially extending links and said first and second circumferentially extending links are enlarged at their intersections to provide pairs of spaced hinges at each connection thereof.

30. A stent according to claim 29 wherein each of said struts extends between at least two axially adjacent linkages.

31. A stent according to claim 30 wherein said axially extending links are perpendicular to said first and second circumferentially extending links.

32. A stent according to claim 31 wherein said enlarged intersections are generally rectangular.

33. A stent having a generally tubular body with a plurality of circumferentially spaced longitudinal struts extending parallel to a longitudinal axis of said body, circumferentially adjacent pairs of said struts being interconnected by a plurality of linkages axially spaced from one another and each including a plurality of links connected to one another, adjacent links of said linkages being angularly disposed relative to one another such that a radial force causes relative rotation between adjacent links and plastic deformation thereof to permit radial expansion of said stent, said struts inhibiting relative axial movement between said linkages and foreshortening of said body and said struts remaining in parallel relationship with said longitudinal axis upon radial expansion of said stent and wherein the intersection of at least one pair of adjacent links of each said linkages has a zone of relative weakness adjacent to but spaced from said intersection to provide a pair of spaced hinge points, whereby relative rotation between said at least one pair of links is distributed between said hinge points.

34. A stent as claimed in claim 33 wherein said intersection of at least one pair of links comprises an enlarged node.

35. A stent as claimed in claim 34 wherein said enlarged node is rectangular.

36. A stent having a generally tubular body with a plurality of circumferentially spaced longitudinal struts extending parallel to a longitudinal axis of said body, circumferentially adjacent pairs of said struts being interconnected by a plurality of linkages axially spaced from one another and each including a plurality of links connected to one another, adjacent links of said linkages being angularly disposed relative to one another such that a radial force causes relative rotation between adjacent links and plastic deformation thereof to permit radial expansion of said stent, said struts inhibiting relative axial movement between said linkages and foreshortening of said body, wherein selected ones of said struts are discontinuous thereby providing a plurality of gaps along the length thereof, the axial location of said gaps being staggered about the circumference of said body whereby relative axial movement between said linkages is inhibited by struts circumferentially spaced from and axially aligned with said gaps, and wherein said gaps are configured to provide only a pair of diametrically aligned struts at selected ones of said axial locations to facilitate flexure of said stent.

37. A stent as claimed in claim 36 wherein said pairs of diametrically aligned struts provide pivot axes of relative pivotal movement between said adjacent linkages.

38. A stent according to claim 37 wherein said pivot axes are angularly disposed relative to one another.

39. A stent according to claim 38 wherein said axes are disposed at 90° to one another.

40. A stent as claimed in claim 39 wherein said diametrically aligned struts are reduced in section.

41. A stent having a generally tubular body with a plurality of circumferentially spaced longitudinal struts extending parallel to a longitudinal axis of said body, circumferentially adjacent pairs of said struts being interconnected solely by a set of linkages axially spaced from one another and defining a predetermined space between adjacent pairs of said struts, all of said sets of linkages being unidirectionally facing and each having a plurality of links angularly disposed relative to one another in an unexpanded condition such that when a radial force is exerted on said tubular body, relative rotation between adjacent links and plastic deformation occurs, thereby increasing said space between said adjacent pairs of sad struts and permitting radial expansion of said stent, said struts inhibiting relative axial movement between said linkages and foreshortening of said body.

42. A stent according to claim 41 wherein each of said linkages includes hinge points spaced apart along said linkage, said hinge points deforming upon radial expansion of said stent to facilitate relative rotation of said links.

43. A stent according to claim 42 wherein said hinge points are provided by zones of relative weakness along said links.

44. A stent according to claim 43 wherein said zones of relative weakness are located adjacent an intersection of adjacent links.

45. A stent according to claim 44 wherein said linkage includes a pair of spaced axial links connected at one end to respective ones of said struts and interconnected at an opposite end by a first circumferential link.

46. A stent according to claim 45 wherein said axial links are perpendicular to said circumferential link in said unexpanded condition.

47. A stent according to claim 46 wherein said axial links are connected to respective ones of said struts by second circumferential links.

48. A stent according to claim 45 wherein said first circumferential link and said axial links intersect at an enlarged node to provide a pair of spaced hinge points adjacent to said node.

49. A stent according to claim 45 wherein opposite ends of said axial link are connected to adjacent links by an enlarged node to provide a pair of spaced hinge points on said axial link.

50. A stent according to claim 45 wherein said first circumferential link is connected at opposite ends to respective axial links by an enlarged node to provide a pair of spaced hinge points on said first circumferential link.

51. A stent having a generally tubular body with a plurality of circumferentially spaced longitudinal struts extending parallel to a longitudinal axis of said body, circumferentially adjacent pairs of said struts being interconnected by a plurality of linkages, each of said linkages having a plurality of links angularly disposed relative to one another and including a pair of axially extending links connected to respective ones of said struts and interconnected to one another at a location spaced axially from their respective connections to said struts, said linkage including at least a pair of links having a portion of reduced cross-section to provide at least three hinge points spaced apart along said linkage and disposed to permit rotation of each of said axially extending links relative to said struts upon application of a radial load to said stent.

52. A stent according to claim 51 wherein said axially extending links are interconnected by a circumferentially extending link.

53. A stent according to claim 52 wherein said circumferentially extending link has a portion of reduced cross-section to provide a pair of circumferentially spaced hinge points adjacent to respective ones of said axial links.

54. A stent according to claim 51 wherein said axially extending links are connected to respective ones of said struts by one of a pair of circumferentially extending links.

55. A stent according to claim 54 wherein said axially extending links are interconnected by a circumferentially extending link.

56. A stent according to claim 55 wherein each of said circumferentially extending links includes a portion of reduced cross-section to provide a pair of spaced hinge points on each of said circumferentially spaced links.

57. A stent according to claim 56 wherein each of said axially extending links includes a portion of reduced cross-section.

58. A stent having a generally tubular body with a plurality of circumferentially spaced longitudinal struts extending parallel to a longitudinal axis of said body, circumferentially adjacent pairs of said struts being interconnected by a plurality of linkages, each of said linkages having a plurality of links angularly disposed relative to one another and including a pair of axially extending links connected to respective ones of said struts and interconnected to one another by a circumferentially extending link, at least a portion of said circumferentially extending link having a reduced cross-section to provide a pair of circumferentially spaced hinge points which, in conjunction with an additional pair of hinge points disposed on said linkage, permit rotation of said axially extending links relative to said circumferentially extending link upon application of a radial load to said body to expand said body.

59. A stent according to claim 58 wherein said additional pair of hinge points is located on respective ones of said axially extending links.

60. A stent according to claim 59 wherein each of said axially extending links has a pair of spaced hinge points formed thereon.

61. A stent according to claim 58 wherein said hinge points plastically deform upon application of a radial load to maintain said body in an expanded condition.

* * * * *